United States Patent [19]

Vardoulakis et al.

[11] Patent Number: 5,024,103
[45] Date of Patent: Jun. 18, 1991

[54] SURFACE INSTABILITY DETECTION APPARATUS

[75] Inventors: Ioannis Vardoulakis, Minneapolis; Joseph F. Labuz; Euripides Papamichos, both of St. Paul, all of Minn.

[73] Assignee: Regents of the University of Minnesota, Minneapolis, Minn.

[21] Appl. No.: 531,111

[22] Filed: May 31, 1990

[51] Int. Cl.$^5$ .............................................. G01N 3/08
[52] U.S. Cl. .................................................... 73/819
[58] Field of Search ................ 73/818, 823, 819, 820, 73/821, 822, 153

[56] References Cited

U.S. PATENT DOCUMENTS

| | | | |
|---|---|---|---|
| 3,505,860 | 4/1970 | Bishop et al. | 73/94 |
| 4,825,700 | 5/1989 | Vardoulakis et al. | 73/749 |
| 4,885,941 | 12/1989 | Vardoulakis et al. | 73/794 |

OTHER PUBLICATIONS

Degtyarenko, G. I. et al. Residual-Stress Measurement ... Mixtures, Ind. Lab (U.S.A.), vol. 44, No. 6 (Jun. '78) (Pub. Dec. '78) pp. 861–862.

*Primary Examiner*—Jerry W. Myracle
*Attorney, Agent, or Firm*—Kinney & Lange

[57] ABSTRACT

A compression test apparatus for geomaterial, such as rock or concrete, samples that is designed to provide measurements of a stress displacement characteristics of the failure zone. A geomaterial formed into a specimen comprising a right rectangular prism is supported by walls along two parallel faces and a back face. An axial load is kinematically applied by a plate that is suitably guided for movement against the specimen which is supported on bottom support plate. All of the surfaces in contact with the specimen are lined with hardened and polished steel plates and lubricated to minimize friction. The assembly of the specimen and its supports is in a conventional loading frame so that an axial load can be applied to one end of the specimen and reacted against the bottom plate. Displacement transducers monitor the lateral displacement of an unrestrained side surface of the specimen.

15 Claims, 4 Drawing Sheets

SURFACE INSTABILITY DETECTION APPARATUS

BACKGROUND OF THE INVENTION

The present invention relates to a surface instability detection apparatus which permits testing samples of geomaterials under axial loads, and in particular, it relates to a surface instability detection apparatus which tests prismatic geomaterial specimens which are restrained and confined on all sides but one.

Surface instability testing of geomaterial, which, for purposes of this application is defined as including, but not limited to, rock and concrete, has been recognized as important in determination of geomaterial characteristics. Geological sample testing apparatus is known wherein what may be termed a selfsupporting geological sample, such as a core of a rock or compacted sand, is subjected to external forces by what is known as a tri-axial testing cell. Normally, hydraulic fluid is introduced in the annular space of a chamber surrounding the sample to apply a hydraulic pressure to the exterior cylindrical surface of the sample. An impermeable membrane usually surrounds the sample being arranged such that the membrane encloses the sample and seals the upper and lower platens to prevent hydraulic fluid gaining access to the ends of the sample.

Geological sample testing has been carried out in the prior art on substantially unrestrained cylindrical core samples in Bishop et al U.S. Pat. No. 3,505,860. The Bishop patent describes a geological sample testing apparatus which includes a chamber with a sample placed between a ram and a platen. A space is left around the sample into which hydraulic fluid is introduced to apply pressure to the sample.

SUMMARY OF THE INVENTION

The present invention relates to an apparatus for testing the surface instability of a geomaterial sample which is under a load. The specimen is formed into a rectangular prism, which is then subjected to an axial load under controlled conditions while the sample is supported in a manner to permit surface displacement along only one surface of the specimen. The specimen is loaded along a longitudinal axis from one end and is slidably retained from displacement along two parallel sides and a back side while permitting displacement along a second axis parallel to the two sides, perpendicular to the back side and perpendicular to the longitudinal axis. One or more displacement transducers monitor the lateral displacements of the front surface of the specimen.

The specimen is loaded by a conventional test loading ram against a base plate of a test load frame. The surfaces of the constraining members for the test specimen are lined with low coefficient of friction, hard surface plates. The lining comprises hardened and polished steel plates which are lubricated to minimize friction. In addition, a front side plate, being substantially parallel and opposite to the back side plate, is preferably disposed in such a manner as to connect the pair of side plates. The front side plate has an aperture formed therethrough to allow the front face of the specimen to move upon failure of the specimen but does have cross bars to assure that the specimen does not fly out of the test load frame. Preferably, a pair of displacement sensors extend through the aperture for sensing displacements of the front surface through the aperture upon a load being applied.

DETAILED DESCRIPTION OF THE PREFERRED EMBODIMENTS

Figure 1:
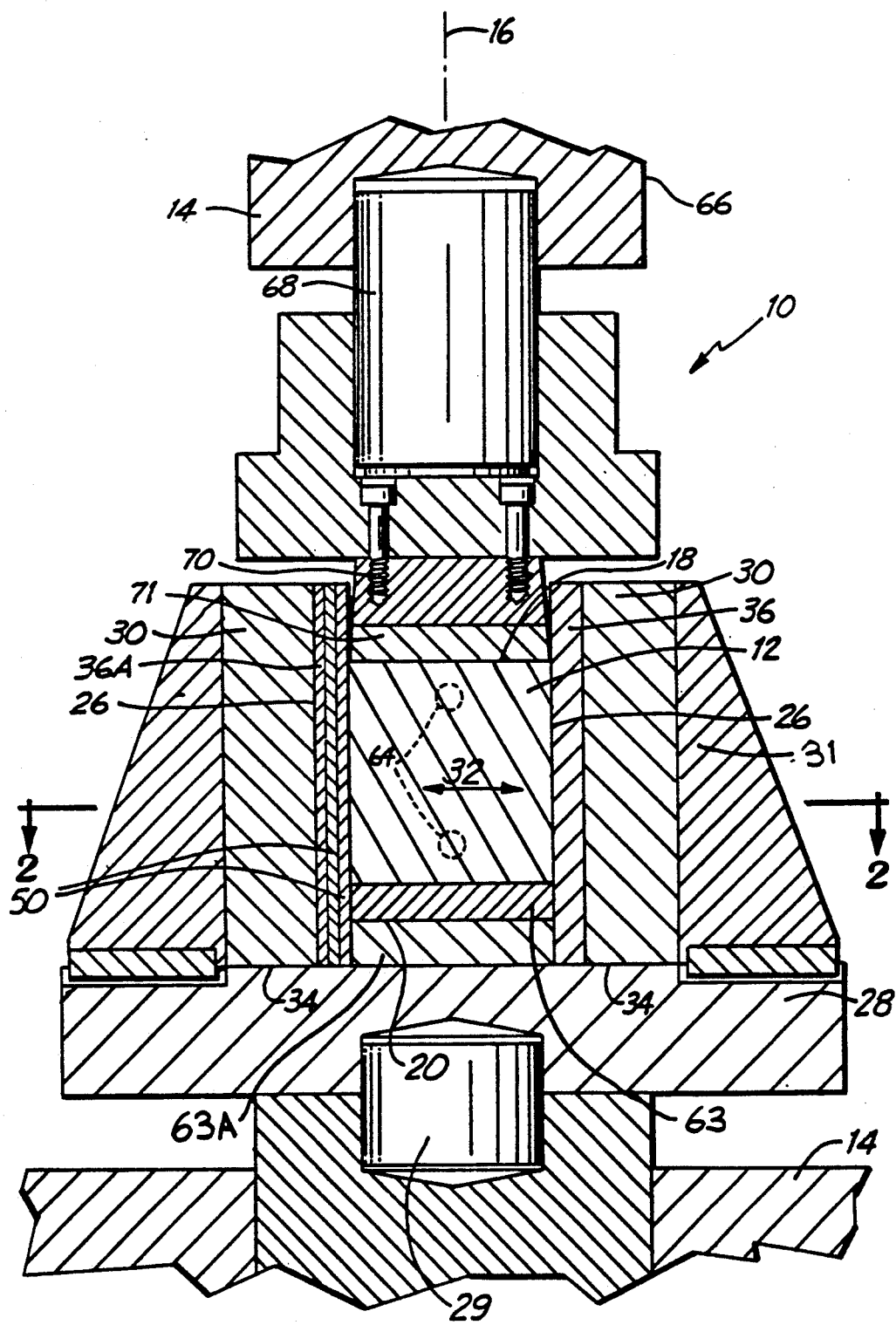
FIG. 1 is a vertical sectional view of a surface instability detection apparatus made according to the present invention shown in a schematically represented test load frame.

The surface instability detection apparatus of the present invention is generally indicated at 10 in FIG. 1. The surface instability detection apparatus 10 supports a specimen 12 in a conventional load frame 14 for testing geomaterial sample specimens, including, but not limited to, rock and concrete, for failure under a load in a direction generally along a central axis 16 of the specimen 12. The load frame 14 is of conventional material test load frame, as is well known in the art. A conventional actuator (shown schematically) forming part of the load frame applies the load onto the specimen 12.

Figure 2:
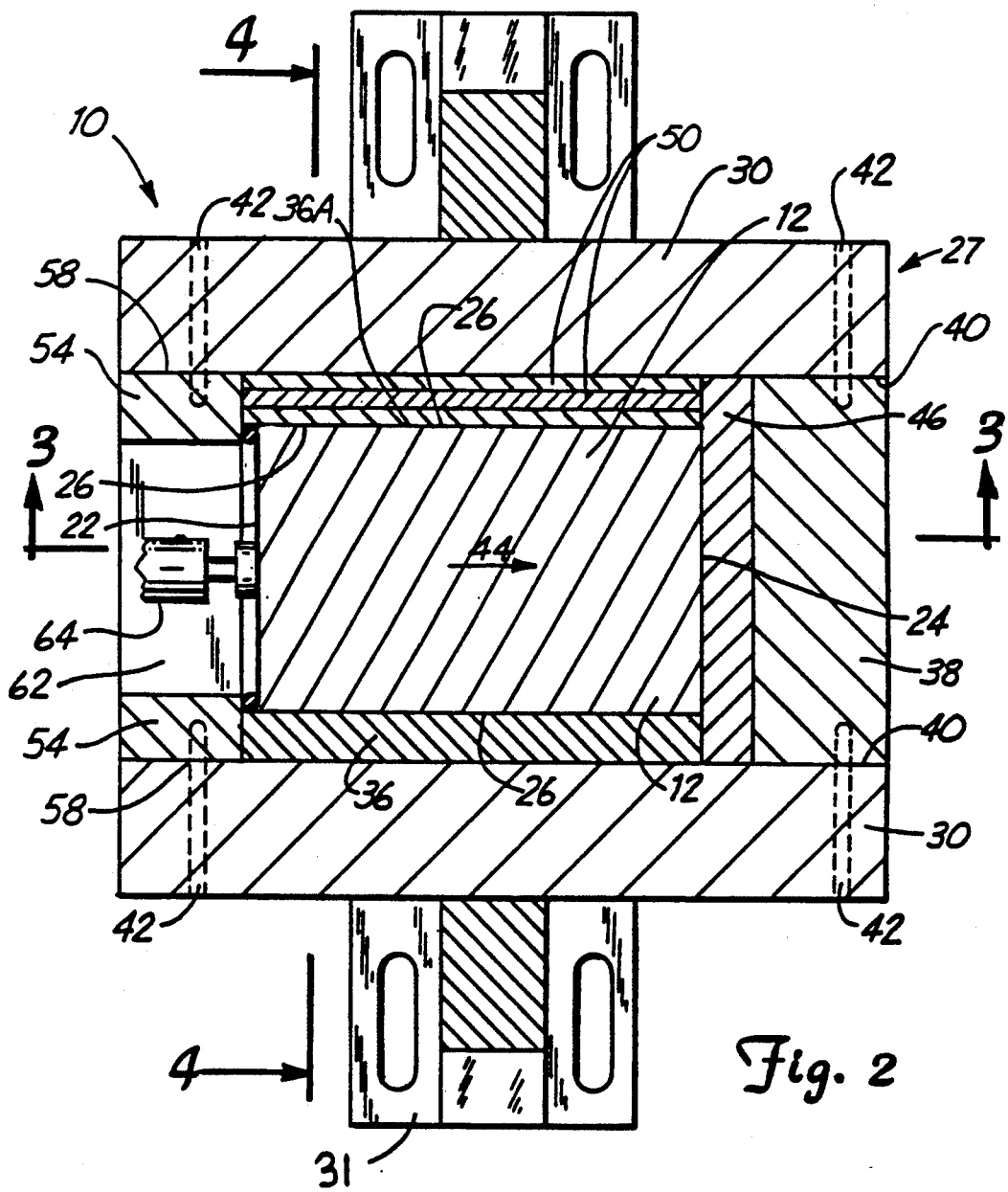
FIG. 2 is a sectional view taken on line 2—2 in FIG. 1.
Figure 3:
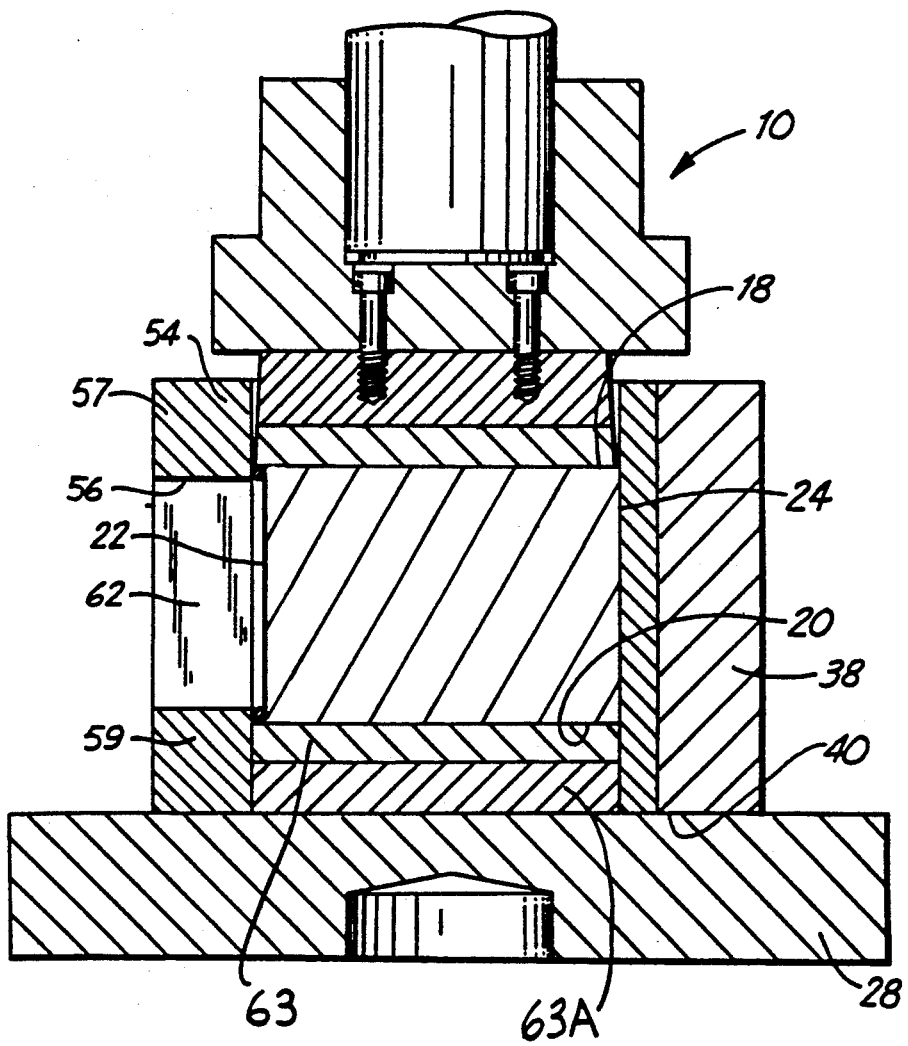
FIG. 3 is a sectional view taken on line 3—3 in FIG. 2.
Figure 4:
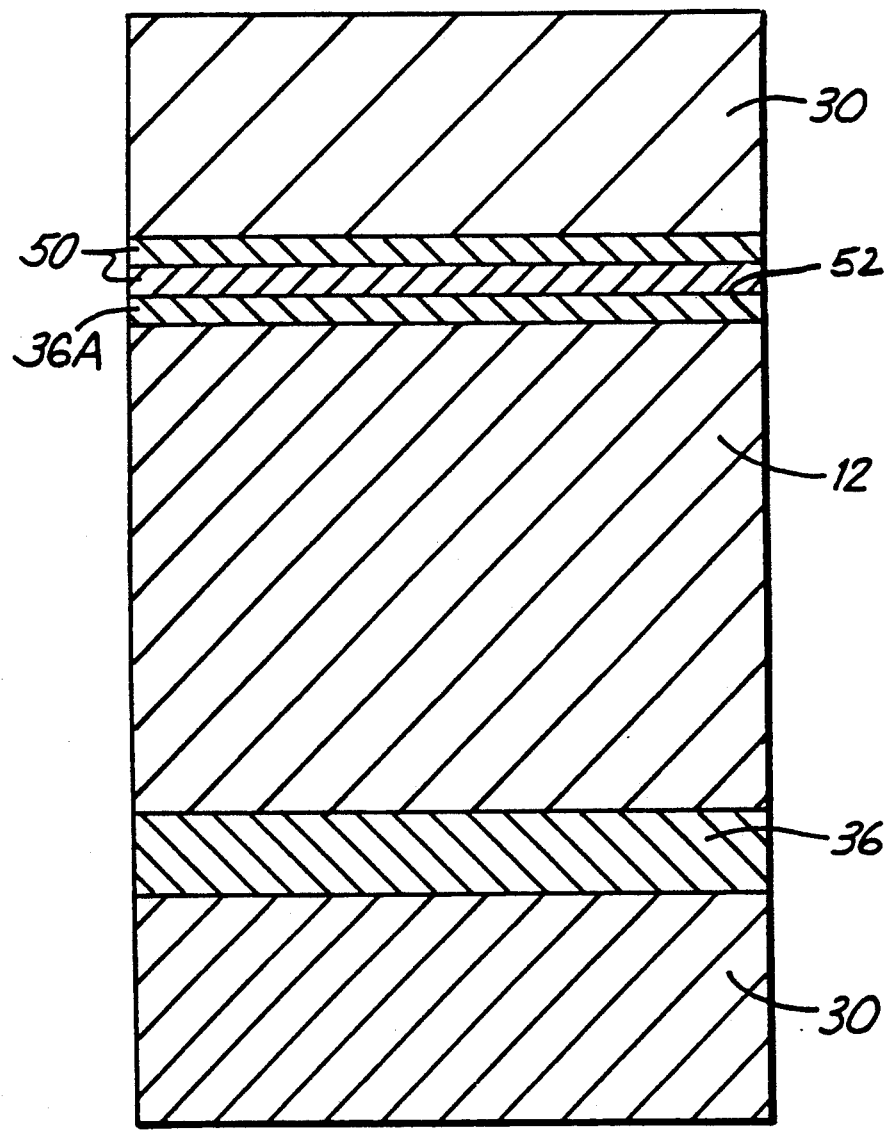
FIG. 4 is an enlarged sectional view taken on line 4—4 in FIG. 2.

The specimen 12 forms generally a right rectangular geometric prism configuration as best shown in FIGS. 2 and 3. The specimen 12 is formed by cutting a geomaterial sample into a rectangular prism by any known method in order to obtain a specimen of the correct dimensions. The dimensions of the specimen can be any size or density depending on the size of the load frame and its limitations. However, the dimensions of the specimen must be of sufficient size to minimize any effect which the boundaries of the fracture mechanism may possess. The preferred dimensions of the specimen are 110 mm (depth), 90 mm (height) and 80 mm (width). In general, the formation of the specimen 12 follows generally known techniques and is not part of the present invention.

The specimen 12 of the present invention has a first end surface 18, a second end surface 20, a front side surface 22, a back side surface 24, and a pair of substantially parallel lateral side surfaces 26. The front side surface 22 and the back side surface 24 are substantially parallel to each other and substantially perpendicular to the lateral side surfaces 26. Furthermore, the first end surface 18 and the second end surface 20 also are substantially parallel to each other and substantially perpendicular to the other surfaces in order to give the specimen 12 a right rectangular prismatic configuration.

In addition to the above, the surface instability detection apparatus 10 of the present invention includes a confinement housing 27 comprising a support plate 28 which supports the specimen 12 during the surface instability testing process. The support plate 28 is supported relative to a cross member of the load frame through a load cell 29. In addition, a pair of upright lateral side plates 30 are fixed to the support plate 28 adjacent to the respective side surfaces 26 of the specimen 12 for restraining movement of the specimen 12 in a lateral directions 32, as illustrated in FIG. 1, perpendicular to the axis 16. The lateral side plates 30 have bases 34 that are at right angles to the plane of the side plates 30 and which rest on plate 28. In addition, side retainers 31 are affixed to the side plates 30 and the support plate 28 in a known manner to enhance the rigidity of the confinement housing 27.

The lateral side plates 30 are fastened with cap screws to the side edges 40 of the back side plate 38. The lateral side plates 30 are securely fastened for maintaining the contiguous side surfaces 26 of the specimen 12 in desired planes and to resist the components of specimen loading forces acting perpendicular to the inner surfaces of the side plates 30. There generally are at least two screws 42 in each of the side edges 40 of the back side plates 38.

One of the lateral side plates 30 is lined with a hardened steel liner plate 36 which bears against the adjacent side surface 26 of specimen 12. A layer of lubricant, including, but not limited to, molybdenum disulfide, is placed between the hardened steel plate 36 and the specimen side surfaces 26 to minimize friction between the specimen 12 and the liner plates 36.

As will be explained, hardened steel wedge plates are positioned between the other side plate 30 and the adjacent surface of the specimen.

An upright back side plate 38 is supported on the support plate 28 and has a side edge surface 40 that is at right angles to the plane of the back side plate 38.

The back side plate 38 constrains the movement of the back side surface 24 of the specimen 12 to be tested in a second lateral direction, indicated by arrow 44, perpendicular to the axis 16 of loading. The back side plate 38 is lined with a hardened steel plate 46 which bears against the back side surface 24 of the specimen 12. A layer of lubricant, which includes, but is not limited to, molybdenum disulfide, is placed between the surface of hardened steel plate 46 and the back side surface 24, to minimize friction between the specimen 12 and the back side plate 38.

After the side plates 30 are securely fastened to back side plate 38 and support plate 28, the entire confinement housing 27 will be prevented from misaligning during the loading process. The back side plate 38 may or may not be attached to the support plate 28, as desired.

In a preferred embodiment of the surface instability detection apparatus 10 of the present invention, a front side plate 54 is provided. The front side plate 54 is opposite from the back side plate 38 and has sides 58 that are at right angles to the plane of the front side plate 54.

Furthermore, the front side plate 54 assists in securely connecting and restraining the side plates 30 with the use of the cap screws 42 which extend through the lateral side plates 30 and into the sides 58 of the front side plate 54. The front plate 54 ties the lateral side plates 30 together for maintaining the side surfaces of the specimen 12 in desired planes and to resist the components of specimen loading forces acting perpendicular to the planes of the side plates 30.

In the preferred embodiment of the present invention, where a front side plate 54 is utilized, an aperture 62 is formed in the front side plate 54 to allow the front side surface 22 of the specimen 12 to move upon failure of the specimen 12. The aperture 62 is preferably in the form of a window, as best illustrated in FIG. 3, and is disposed such that a top edge 56 is lower than the top of the specimen 12. This configuration provides top and bottom cross bars 57 and 59 which prevent the specimen 12 from "shooting out" of the housing 27 upon the application of a load, while still allowing the determination and detection of front surface instability.

The specimen 12 is then placed within the housing 27 such that the specimen 12 rests upon a hardened steel plate 63 which is supported on a block 63A which is on the support plate 28. The specimen is held between the lateral side plates 30 and the back side plate 38. It is important to make sure that the specimen 12 has been prepared and sized such that the specimen 12 fits within the housing 27 with little or no space between the specimen 12 and the lateral side plates 30 and the back side plate 38.

Shims or wedges 50 are used to assure a snug and tight fit of the specimen 12 within the housing 27. The shims 50 are preferably wedged between one of the lateral side plates 30 and a thinner flat-sided liner plate 36A resting against the specimen 12 on the side opposite from liner plate 36 to urge the specimen 12 toward the opposite liner plate 36 and lateral side wall 30 and snugly hold the specimen 12 within the housing 27. The shims 50 are generally trapezoidal-shaped in cross-section and are fitted together as a pair such that the sides of the two wedges 50, are substantially parallel to the plane of the lateral side plates 30. The shims 50 may be of any desired thickness depending on the cut size of the specimen 12 relative to the spacing of the lateral side plates 30. More than one set of shims 50 of different thicknesses may be used depending on the machined-size of the specimen 12. The shims 50 may also have hardened steel surfaces 52 and can be lubricated to serve as friction reducing plates. If this is the case, the liner plate 36A is not necessary.

The front side surface 22 of the specimen 12 is substantially unrestrained. By allowing the front side surface 22 to be unrestrained while securely restraining the side surfaces 26 and the back side surface 24, any failure which occurs along the specimen 12 during a loading process, occurs in the front side surface 22 of the specimen 12. This design and configuration of forcing failure to occur only on the front side surface 22 allows the user to determine and detect the surface instability of a geomaterial specimen in the safety of a laboratory setting.

A plurality of displacement sensors 64 extend through the aperture 62 and bear against the front side surface 22 of the specimen 12 for sensing movement or displacements of the front side surface 22. The movement of the specimen 12 in the direction of the aperture 62 is sensed by the linear displacement sensors. As shown in FIGS. 2 and in dotted lines in FIG. 1, a pair of linear displacement sensors 64 are mounted on the housing 27 in a suitable manner and have sensing members positioned on the front side surface 22 to sense movements of the specimen substantially parallel with the plane of the side plates 30.

An actuator shown schematically at 66 loads the specimen 12 on the second end surface 18 under a load directed toward the support plate 28 along the central axis 16 of the specimen 12. The actuator 66 loads through a load cell 68 and suitable bearing plates 70 and 71 slide between the wedges 50 and plate 36 to load the specimen 12. The loading sequence uses conventional loading techniques. The load is applied until the specimen 12 fails.

A vertical displacement sensor is provided to measure the vertical displacement along the central axis 16 of the specimen 12. The vertical displacement sensor in the present design is internally mounted in the actuator 66 of the load frame.

The low friction hardened steel plates on all sides of the specimen 12 (except the face where failure occurs) used for contacting the specimen 12 can be polished smooth, and any scratches or other imperfections can be easily seen and polished down so they do not tend to increase the resistance to shifting of portions of the specimen 12 as it fails.

Although the present invention has been described with reference to preferred embodiments, workers skilled in the art will recognize that changes may be made in form and detail without departing from the spirit and scope of the invention.

What is claimed is:

1. A surface instability detection apparatus for supporting a specimen in a load frame for testing geomaterial sample specimens for failure under load in a direction generally along a central axis of the specimen, the specimen having first and second end surfaces, front and back side surfaces, and a pair of substantially parallel lateral side surfaces, the specimen forming generally a right rectangular geometric prism configuration, the apparatus comprising:

a support plate supporting a first end surface of the specimen;
a pair of lateral side plates fixed with respect to the support plate and the adjacent two opposite lateral side surfaces of the specimen for restraining movement of the specimen in first lateral directions perpendicular to the axis;
means for loading such specimen on a second end surface under a load directed toward the support plate along the central axis of the specimen until such specimen fails;
a back side plate mounted relative to the support plate and the lateral side plates for restraining movement of the back side surface of the specimen to be tested in a second lateral direction perpendicular to the axis of loading, the back side plate being disposed in such a manner as to connect the pair of lateral side plates; and
the front side surface of the specimen being substantially unrestrained whereby upon loading of the specimen, the specimen is forced to fail by movement of the front side surface only.

2. The apparatus as specified in claim 1 and a front side plate, the front side plate being substantially parallel and opposite to the back side plate and disposed in such a manner as to connect the pair of lateral side plates.

3. The apparatus as defined in claim 2 wherein the front wall has an upper edge lower than the specimen for preventing the specimen from moving away from the back side plate in a direction substantially parallel to the lateral side plates.

4. The apparatus as specified in claim 1 and an aperture formed in the front side plate to allow the front face of the specimen to move upon failure of the specimen.

5. The apparatus as specified in claim 4 and displacement sensor means extending through the aperture for sensing displacements of the front side surface through the aperture.

6. The apparatus as specified in claim 1 and first sensor means for sensing loads on the support plate in a direction along the support axis.

7. The apparatus as specified in claim 1 and a vertical displacement sensor means mounted to the loading means such that the vertical displacement sensor measures the vertical displacement along the central axis of the specimen.

8. The apparatus as specified in claim 1 and liner plates positioned to line the back and lateral side walls to provide surfaces in contact with the specimen.

9. The apparatus as specified in claim 8 wherein the liner plates comprise hardened and polished steel plates, the steel plates being lubricated to minimize friction loads on the specimen.

10. A test apparatus for supporting a specimen in a load frame for testing geomaterial sample specimens for failure under load in a direction generally along a central axis of the specimen, the specimen having first and second end surfaces, and first, second, third and fourth side surfaces, the specimen forming generally a right rectangular geometric prism configuration, the apparatus comprising:

a support plate supporting a first end surface of the specimen;
first and second side plates fixed with respect to the support plate adjacent two opposite side surfaces of the specimen for restraining movement of the specimen in first lateral directions perpendicular to the axis;
means for loading such specimen on a second end surface under a load directed toward the support plate along the central axis of the specimen until such specimen fails;
a third side plate mounted relative to the support plate and the first and second side plates for restraining movement of a facing side surface of the specimen to be tested in a second lateral direction perpendicular to the axis of loading, the third side plate being disposed in such a manner as to connect the first and second side plates;
one side surface of the specimen being substantially unrestrained whereby upon loading of the specimen, the specimen is forced to fail by movement of the one side surface only.

11. The apparatus of claim 10 and a fourth side plate, the fourth side plate being substantially parallel and opposite to the third side plate and disposed in such a manner as to connect the first and second side plates.

12. The apparatus of claim 11 and an aperture formed in the fourth side plate to allow the adjacent face of the one side surface of the specimen to move upon failure of the specimen.

13. The apparatus of claim 12 wherein the fourth side plate has an edge below the level of the specimen for preventing the specimen from moving away from the third side plate in a direction substantially parallel to the first and second side plates.

14. A test apparatus for supporting a specimen in a load frame for testing geomaterial sample specimens for failure under load in a direction generally along a central axis of the specimen, the specimen having first and second end surfaces, and side surfaces to form a geometric prism configuration, the apparatus comprising:

a support plate supporting a first end surface of the specimen;
side plates fixed with respect to the support plate adjacent opposite sides of the specimen for restraining movement of the specimen in selected lateral directions perpendicular to the axis;
means for loading such specimen in compression tending to move the first and second end surfaces together; and at least a substantial portion of a side of the specimen being substantially unrestrained by side plates whereby upon loading of the specimen, the specimen is forced to fail by movement of the unrestrained portion of the side only.

15. The apparatus of claim 14 wherein side plates surround the specimen and an aperture formed in the side plates to allow the substantial portion of the side of the specimen that is unrestrained to move through the aperture upon failure of the specimen.

* * * * *